United States Patent
Petrov

(10) Patent No.: US 9,946,073 B2
(45) Date of Patent: Apr. 17, 2018

(54) METHODS AND SYSTEMS FOR ELIMINATING STROBING BY SWITCHING DISPLAY MODES IN RESPONSE TO DETECTING SACCADES

(71) Applicant: OCULUS VR, LLC, Menlo Park, CA (US)

(72) Inventor: Yury Anatolievich Petrov, Half Moon Bay, CA (US)

(73) Assignee: OCULUS VR, LLC, Menlo Park, CA (US)

( * ) Notice: Subject to any disclaimer, the term of this patent is extended or adjusted under 35 U.S.C. 154(b) by 163 days.

(21) Appl. No.: 14/985,797

(22) Filed: Dec. 31, 2015

(65) Prior Publication Data
US 2017/0192235 A1  Jul. 6, 2017

(51) Int. Cl.
*G09G 5/00* (2006.01)
*G02B 27/01* (2006.01)
*A61B 3/113* (2006.01)

(52) U.S. Cl.
CPC .......... *G02B 27/0172* (2013.01); *A61B 3/113* (2013.01); *G02B 27/0101* (2013.01); *G02B 27/017* (2013.01); *G02B 2027/014* (2013.01); *G02B 2027/0187* (2013.01)

(58) Field of Classification Search
CPC .............. G02B 27/0172; G02B 27/017; G02B 27/0101; G02B 2027/0187; G02B 2027/014; A61B 3/113
See application file for complete search history.

(56) References Cited

U.S. PATENT DOCUMENTS

2013/0293844 A1\* 11/2013 Gross ................... A61B 3/0025
351/209
2017/0068312 A1\* 3/2017 Mallinson ............... G06F 3/013

\* cited by examiner

*Primary Examiner* — Jonathan Boyd
(74) *Attorney, Agent, or Firm* — Morgan, Lewis & Bockius LLP

(57) ABSTRACT

A virtual-reality system includes a head-mounted display system comprising an eye tracker and a display screen comprising an array of pixels. The virtual-reality system monitors movement of a user's eye using the eye tracker. A first plurality of frames for virtual-reality images is displayed on the display screen using a first persistence in accordance with a first display mode. The persistence is a percentage of a frame duration during which the array of pixels is activated. While displaying the first plurality of frames in accordance with the first display mode, a saccade of the user's eye is detected. In response to detecting the saccade, the virtual-reality system switches from the first display mode to a second display mode having a second persistence that is greater than the first persistence. In the second display mode, a second plurality of frames for the virtual-reality images is displayed using the second persistence.

20 Claims, 6 Drawing Sheets

METHODS AND SYSTEMS FOR ELIMINATING STROBING BY SWITCHING DISPLAY MODES IN RESPONSE TO DETECTING SACCADES

TECHNICAL FIELD

This application relates generally to wearable technology and virtual-reality technology, including but not limited to eliminating strobing by switching display modes in response to detecting a saccade.

BACKGROUND

Virtual-reality systems have wide applications in various fields, including engineering design, medical surgery practice, military simulated practice, and video gaming. Display screens used in virtual-reality systems are normally driven at low persistence, where screen persistence is the percentage of a video frame duration during which pixels of the display screen are actually lit. Low persistence, such as 10% to 20%, is typically used for moderate (e.g., 75-120 Hz) screen refresh rates to avoid image blurring during head rotations.

However, a side effect of using screens at low persistence is strobing, where multiple copies of a visual object are perceived simultaneously. Strobing is most noticeable during fast eye movements, known as saccades. During a saccade, when images are displayed using low persistence, copies of objects corresponding to different video frames are "imprinted" on the retina. In the case of a periodic structure that is made of such objects, such as a linear grid, strobing can result in visual instability where the brain fails to correctly match objects to themselves between successive video frames. The resulting sense of disorientation and illusory motion is often discomforting. Using display screens at higher persistence would require significantly faster refresh rates to avoid image blurring. With many display technologies, however, such high frequency refresh rates are not feasible.

SUMMARY

Accordingly, there is a need for methods, systems, and devices for switching display modes in response to detecting a saccade in order to eliminate strobing. By monitoring movement of a user's eye while displaying virtual-reality images, a virtual-reality system may switch from one display mode to another having a higher persistence in response to detecting a sufficiently fast saccade. By using a higher persistence throughout the saccade and switching back to a lower persistence when the saccade ends, both the negative effects of strobing and image blurring are reduced (e.g., minimized).

In accordance with some embodiments, a method is performed at a virtual-reality system that includes a head-mounted display system comprising an eye tracker and a display screen comprising an array of pixels. The method includes monitoring movement of a user's eye, using the eye tracker. A first plurality of frames for virtual-reality images is displayed on the display screen using a first persistence in accordance with a first display mode. The persistence is a percentage of a frame duration during which the array of pixels of the display screen is activated. While displaying the first plurality of frames in accordance with the first display mode and while monitoring movement of the user's eye, a saccade of the user's eye is detected. In response to detecting the saccade, the method includes switching from the first display mode to a second display mode having a second persistence that is greater than the first persistence. In the second display mode, a second plurality of frames for the virtual-reality images is displayed using the second persistence.

In accordance with some embodiments, a virtual-reality system includes a head-mounted display system comprising an eye tracker and a display screen comprising an array of pixels. The virtual-reality system further includes one or more processors and memory storing one or more programs for execution by the one or more processors. The one or more programs include instructions for performing the operations of the method described above. In accordance with some embodiments, a non-transitory computer-readable storage medium has stored therein instructions that, when executed by the virtual-reality system, cause the virtual-reality system to perform the operations of the method described above.

Thus, systems, devices, and methods are provided with effective methods for reducing or eliminating strobing while displaying virtual-reality images, thereby increasing user satisfaction with such systems and devices.

BRIEF DESCRIPTION OF THE DRAWINGS

For a better understanding of the various described embodiments, reference should be made to the Description of Embodiments below, in conjunction with the following drawings. Like reference numerals refer to corresponding parts throughout the figures and description.

DESCRIPTION OF EMBODIMENTS

Reference will now be made to embodiments, examples of which are illustrated in the accompanying drawings. In the following description, numerous specific details are set forth in order to provide an understanding of the various described embodiments. However, it will be apparent to one of ordinary skill in the art that the various described embodiments may be practiced without these specific details. In other instances, well-known methods, procedures, components, circuits, and networks have not been described in detail so as not to unnecessarily obscure aspects of the embodiments.

It will also be understood that, although the terms first, second, etc. are, in some instances, used herein to describe various elements, these elements should not be limited by these terms. These terms are used only to distinguish one element from another. For example, a first display mode could be termed a second display mode, and, similarly, a second display mode could be termed a first display mode, without departing from the scope of the various described embodiments. The first display mode and the second display mode are both display modes, but they are not the same display mode.

The terminology used in the description of the various embodiments described herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" is, optionally, construed to mean "when" or "upon" or "in response to determining" or "in response to detecting" or "in accordance with a determination that," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]" or "in accordance with a determination that [a stated condition or event] is detected," depending on the context.

As used herein, the term "exemplary" is used in the sense of "serving as an example, instance, or illustration" and not in the sense of "representing the best of its kind."

Figure 1A:
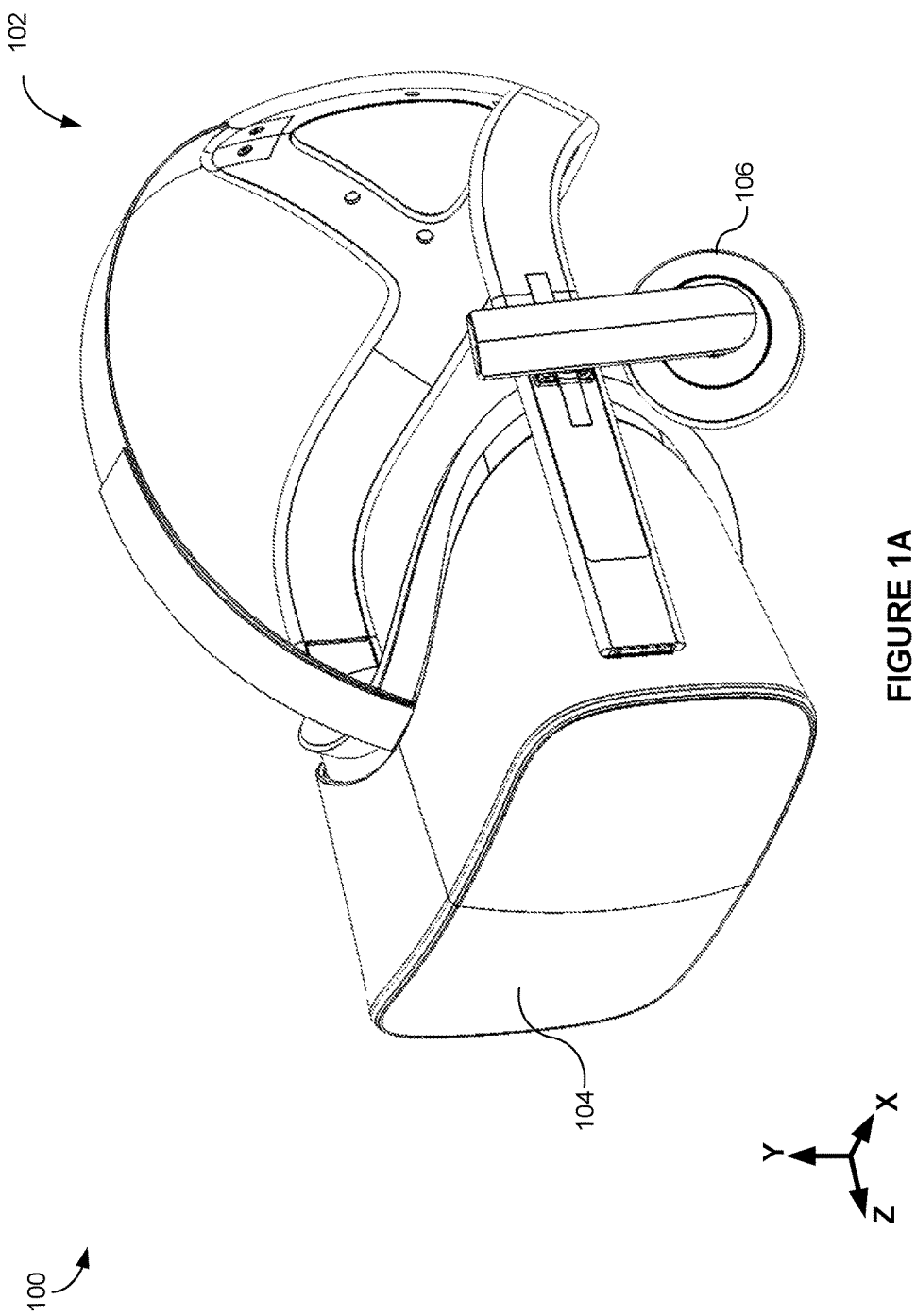
FIG. 1A is a perspective view of a head-mounted display in a virtual-reality system, in accordance with some embodiments.
Figure 1B:
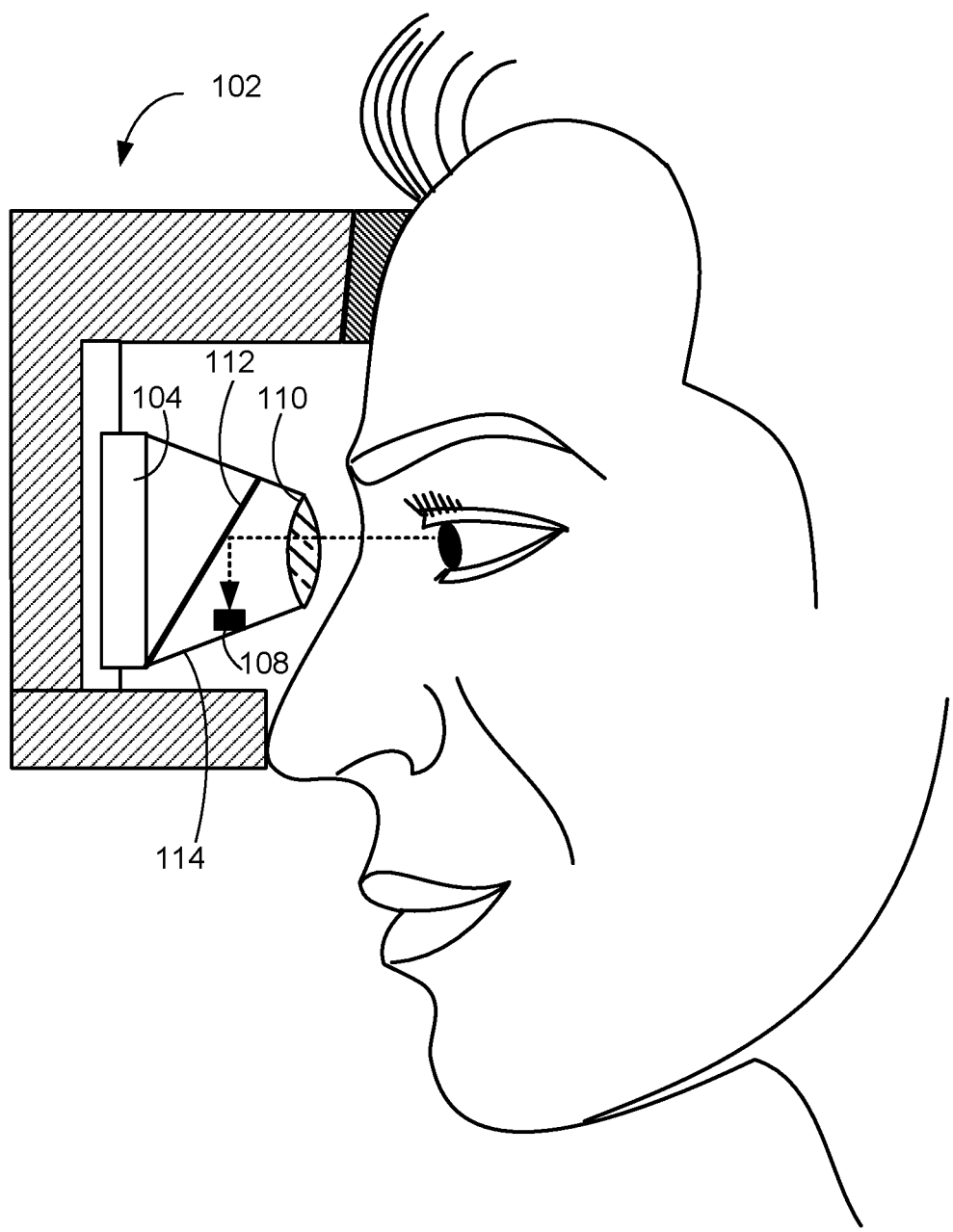
FIG. 1B is a side view of a head-mounted display in a virtual-reality system, in accordance with some embodiments.

FIGS. 1A and 1B are various views of a head-mounted display system 102 in a virtual-reality system 100, in accordance with some embodiments.

FIG. 1A is a perspective view of a the head-mounted display system 102, which includes a display 104, audio output 106, an eye tracker 108 (FIG. 1B), and optional optical components (e.g., lens 110, mirror 112, eye cup 114, etc., described with respect to FIG. 1B).

Images rendered on the display 104 provide a virtual-reality experience to a user wearing the head-mounted display system 102. To reduce image blurring during head rotations, images are displayed on the head-mounted display system 102 using a low persistence, where persistence is the percentage of a frame duration during which pixels of the display 104 are activated. However, displaying images using low persistence can sometimes lead to a strobing effect in which the user experiences visual instability between successive video frames. The strobing effect is most noticeable during fast user eye movements, known as saccades. In order to reduce or avoid the negative effects of strobing, the eye tracker 108 monitors movement of the user's eye while virtual-reality images are displayed. When a saccade satisfying a threshold is detected, the head-mounted display system 102 switches to a different display mode in which images are displayed using a greater persistence. As a result of using a greater persistence during the duration of the saccade, strobing effects experienced by the user are reduced or eliminated. Switching between display modes and persistence levels is described with respect to FIGS. 3A-3C.

The display 104 comprises an array of pixels for displaying rendered images. In some embodiments, the display 104 is based on organic light-emitting diode (OLED) technology. In some embodiments, the display 104 operates in accordance with a refresh rate specifying a number of video frames displayed per unit of time and a corresponding frame duration (e.g., for a refresh rate of 100 Hz, 100 frames are displayed per second, and the frame duration is 10 ms). Furthermore, pixels of the display 104 are activated and illuminated in accordance with a specified persistence (e.g., a percentage of a frame duration during which pixels of the display 104 are activated).

In some embodiments, the virtual-reality system 100 includes optional devices or components for providing the virtual-reality experience. For example, the virtual-reality system 100 may include a computing device (not shown), distinct from the head-mounted display system 102, for rendering images, video, or other multimedia. In some embodiments, the virtual-reality system 100 includes one or more sensors (e.g., gyroscopes, accelerometers) which obtain and provide sensor readings for use in image or video rendering. In some embodiments, various electrical connection mechanisms (e.g., flat flexible circuits and/or electric cables) are used in the head-mounted display system 100 to provide power management, signal transmission, and/or other functionalities.

FIG. 1B is a side view of a virtual-reality system 100. As illustrated, the head-mounted display system 102 includes a display 104, lens 110, and eye cup 114 coupling the lens 110 to the display 104. Furthermore, the eye cup 114 includes an eye tracker 108 and a mirror 112 for monitoring eye movements of a user in order to detect saccades. The head-mounted display system 102 may include a separate display 104, lens 110, eye cup 114, eye tracker 108, and/or mirror 112 for each eye.

As mentioned above, the eye tracker 108 monitors movement of the user's eye while displaying virtual-reality images in order to detect a saccade for switching display modes. In some embodiments, in order to monitor such movement, infrared light is emitted (e.g., from a light source within the head-mounted display system 102, not illustrated) and directed towards a user's eye. The infrared light that is reflected off the user's eye is then reflected off the mirror 112, which is configured to reflect infrared light and transmit visible light. The infrared light is therefore reflected into the eye tracker 108 and processed. In some embodiments, the eye tracker 108 obtains various measurements for the reflected infrared light (e.g., magnitude of light intensity, direction of reflected light, rate of change of intensity/direction, etc.), which may be used to determine an eye's degree of rotation, a user's direction of gaze, and/or other ocular characteristics. Other eye-monitoring technologies may be additionally or alternatively implemented. Furthermore, while the eye tracker 108 in this example is disposed along and connected to the inside border of the eye cup 114, the eye tracker may alternatively be positioned outside of the eye cup (e.g., below the eye cup, positioned along the rim of the head-mounted display system 102).

The eye tracker 108 obtains measurements corresponding to detected eye movement in accordance with a sampling rate (e.g., 240 Hz). In some embodiments, the speed with which a saccade is detected (e.g., from the beginning of the saccade) is based on the sampling rate (e.g., the faster the sampling rate, the more quickly a saccade is detected). In some embodiments, the sampling rate of the eye tracker 108 is greater than the refresh rate of the display 104.

As described in greater detail below, in some embodiments, the beginning and end of saccades satisfying specified thresholds cause the virtual-reality system 100 to switch display modes. The specified threshold may be a movement threshold (e.g., an angle through which a user's eye moves during a specified period of time, a speed of the user's eye, etc.) and/or a threshold duration (e.g., a duration of a saccade).

Figure 2:
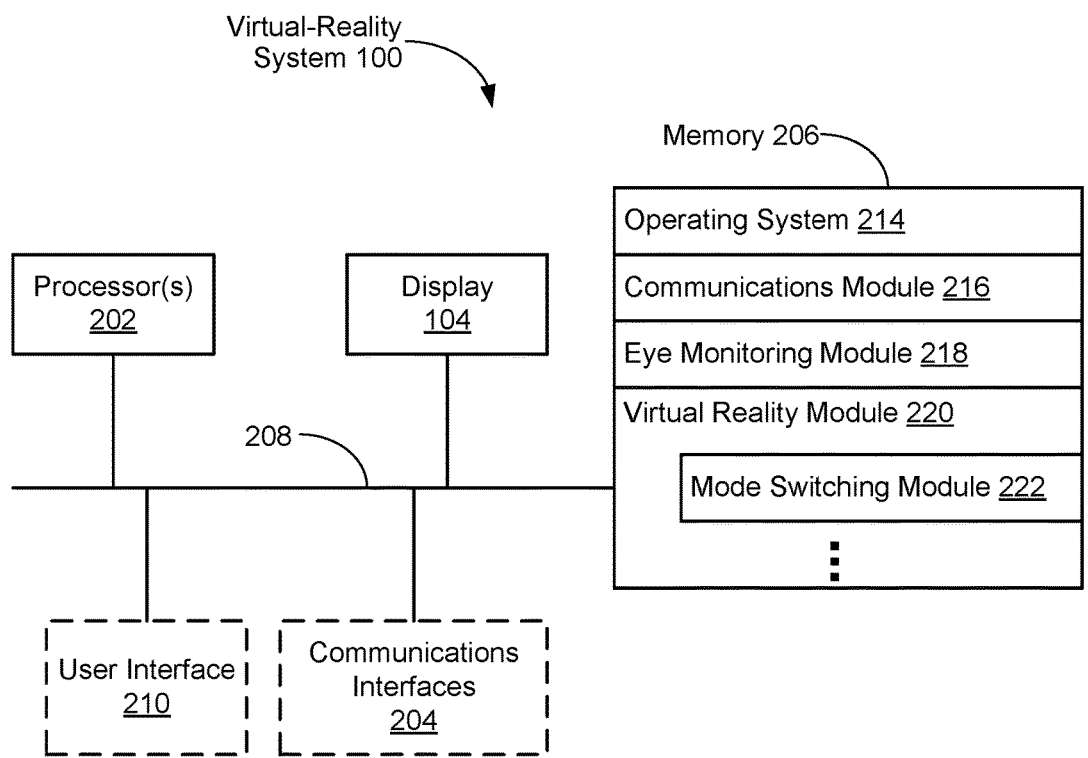
FIG. 2 is an electrical block diagram illustrating a virtual-reality system, in accordance with some embodiments.

FIG. 2 is a block diagram illustrating a virtual-reality system 100, in accordance with some embodiments. The virtual-reality system 100 typically includes one or more processing units (processors or cores) 202, one or more optional network or other communications interfaces 204, memory 206, and one or more communication buses 208 for interconnecting these components. The communication buses 208 optionally include circuitry (sometimes called a chipset) that interconnects and controls communications between system components. The virtual-reality system 100 includes a display 104 (i.e., in the head-mounted display system 102) and optional output devices (e.g., audio output 106, FIG. 1A). Furthermore, the virtual-reality system 100 includes an optional user interface 210 (e.g., a hand-held controller with a thumbstick and input buttons).

Memory 206 includes high-speed random-access memory, such as DRAM, SRAM, DDR RAM or other random-access solid-state memory devices; and may include non-volatile memory, such as one or more magnetic disk storage devices, optical disk storage devices, flash memory devices, or other non-volatile solid-state storage devices. Memory 206 may optionally include one or more storage devices remotely located from the processor(s) 202. Memory 206, or alternately the non-volatile memory device (s) within memory 206, includes a non-transitory computer-readable storage medium. In some embodiments, memory 206 or the computer-readable storage medium of memory 206 stores the following programs, modules and data structures, or a subset or superset thereof:
- an operating system 214 that includes procedures for handling various basic system services and for performing hardware dependent tasks;
- a network communication module 216 that is used for communicably connecting the virtual-reality system 100 to other computers or devices via the one or more communication network interfaces 204 (wired or wireless);
- an eye monitoring module 218 for monitoring movement of a user's eye (e.g., an angle moved during a specified time period) and determining whether detected saccades satisfy one or more thresholds (e.g., movement threshold, threshold duration, etc.); and
- a virtual reality module 220 for accessing, manipulating, rendering, and/or displaying virtual content (e.g., a virtual-reality session), where virtual content is displayed in accordance with a refresh rate (e.g., 120 Hz) and using a specified persistence (e.g., 10% of a frame duration), including the following modules (or sets of instructions), or a subset or superset thereof:
  - a mode switching module 222 for switching (e.g., in response to detecting a saccade) between display modes having respective persistence settings (e.g., switch from using 10% persistence to 50% persistence).

Each of the above identified modules and applications correspond to a set of executable instructions for performing one or more functions as described above and/or in the methods described in this application (e.g., the computer-implemented methods and other information processing methods described herein). These modules (i.e., sets of instructions) need not be implemented as separate software programs, procedures or modules, and thus various subsets of these modules are, optionally, combined or otherwise re-arranged in various embodiments. In some embodiments, one or more components of the virtual-reality system 100 (e.g., head-mounted display system 102, display 104, eye tracker 108, etc.) have one or more respective processors and respective memories storing executable instructions corresponding to any one or combination of modules described with respect to memory 206. Memory 206 optionally stores additional modules and data structures not described above.

Figure 3A:
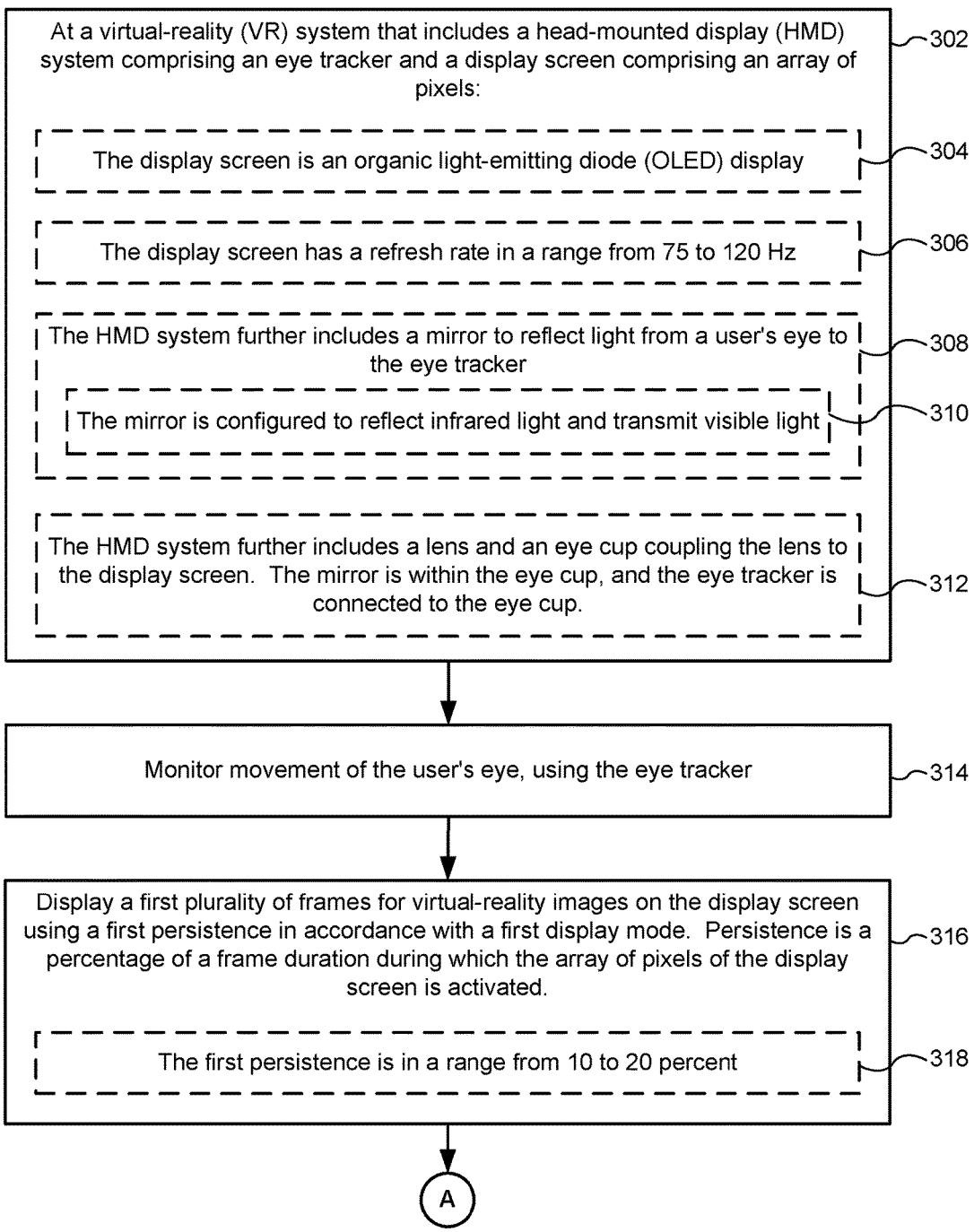
FIGS. 3A-3C are flow diagrams illustrating a method of reducing or eliminating strobing by switching display modes in response to detecting a saccade, in accordance with some embodiments.
Figure 3B:
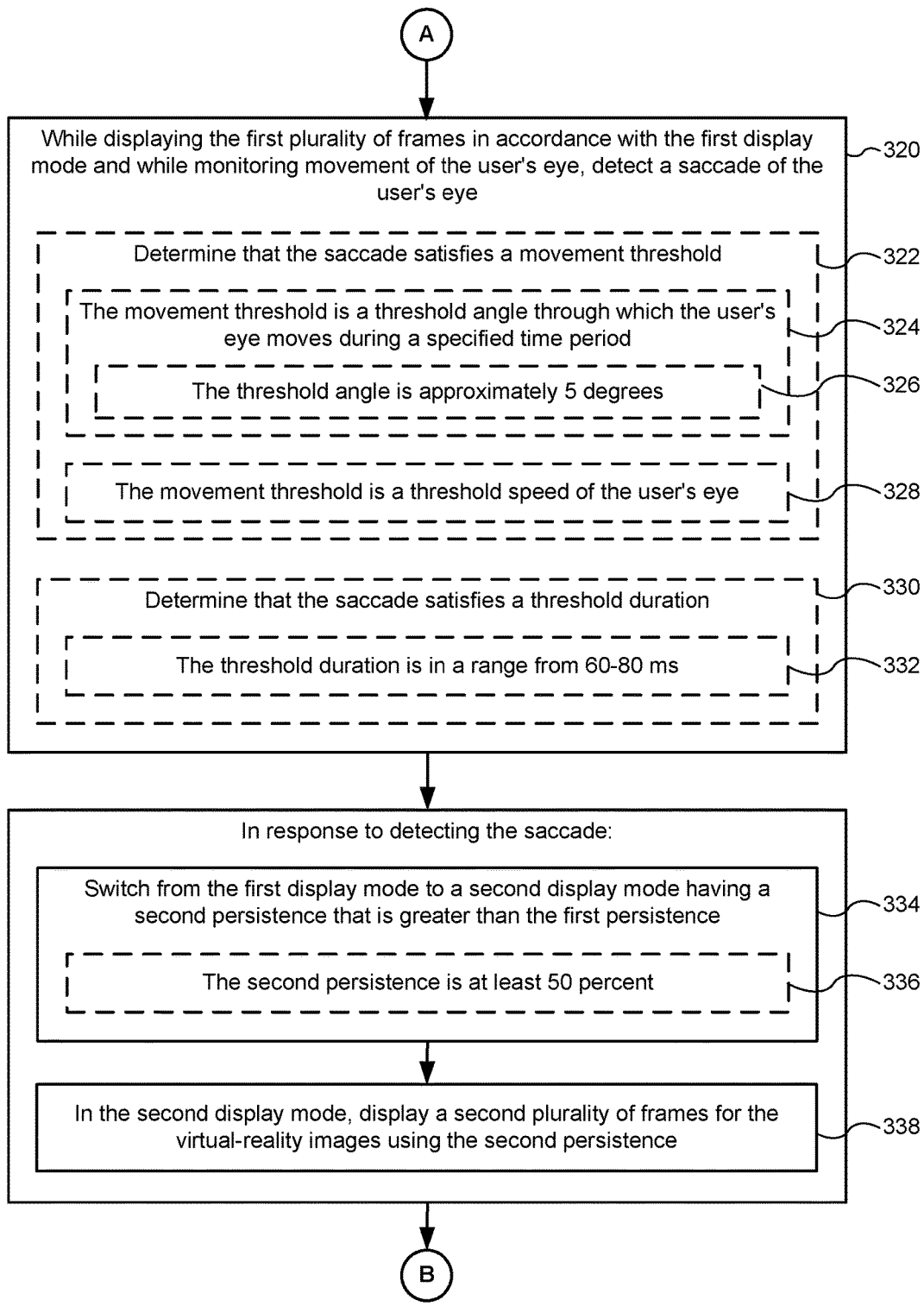
Figure 3C:
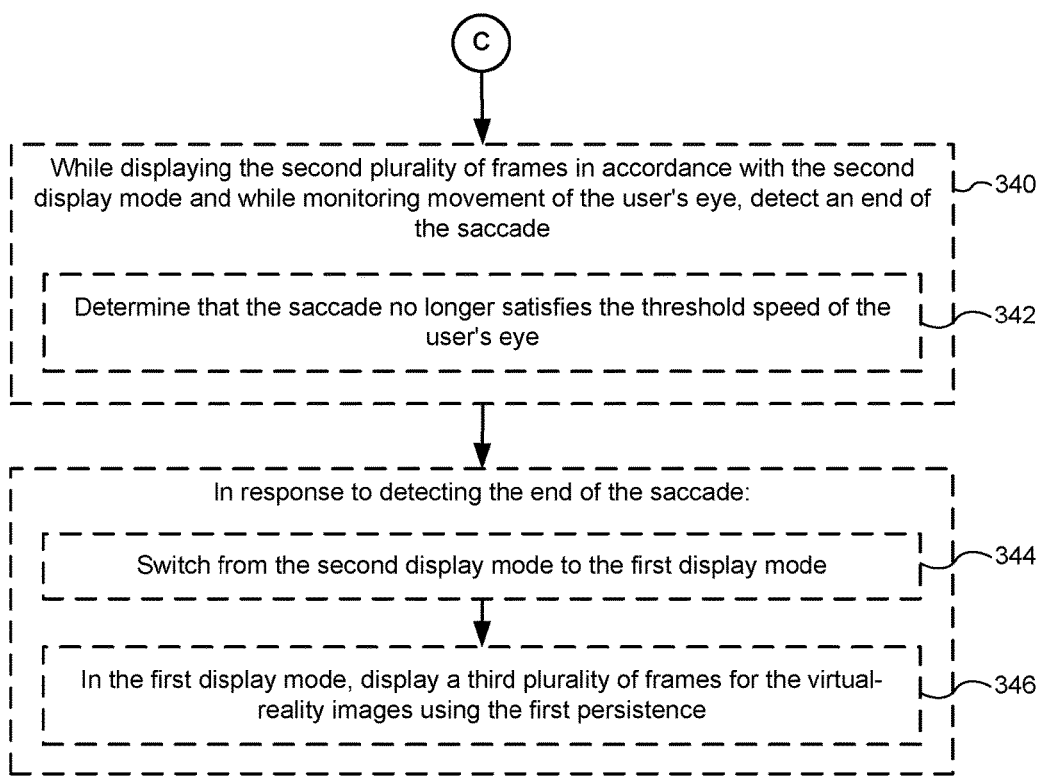

FIGS. 3A-3C are flow diagrams illustrating a method 300 of eliminating strobing by switching display modes in response to detecting a saccade, in accordance with some embodiments.

The method 300 is performed (302) at a virtual-reality (VR) system (e.g., virtual-reality system 100, FIGS. 1A. 1B. and 2) that includes a head-mounted display (HMD) system (e.g., head-mounted display system 102) comprising an eye tracker (e.g., eye tracker 108, FIG. 1B) and a display screen (e.g., display 104) comprising an array of pixels. Steps of the method 300 may be performed by one or more components of the virtual-reality system (e.g., head-mounted display system 102, display 104, eye tracker 108, etc.). Furthermore, steps of the method 300 correspond to instructions stored in respective memory (and are performed by respective processor(s)) of the one or more components that perform the steps.

In some embodiments, the display screen is (304) an organic light-emitting diode (OLED) display. In some embodiments, the display screen has (306) a refresh rate in a range from 75 to 120 Hz.

In some embodiments, the HMD system further includes (308) a mirror (e.g., mirror 112, FIG. 1B) to reflect light from a user's eye to the eye tracker. In some embodiments, the mirror is configured (310) to reflect infrared light and transmit visible light.

In some embodiments, the HMD system further includes (312) a lens (e.g., lenses 110, FIG. 1B) and an eye cup (e.g., eye cup 114, FIG. 1B) coupling the lens to the display screen. The mirror is within the eye cup, and the eye tracker is connected to the eye cup.

The VR system monitors (314) movement of the user's eye, using the eye tracker (e.g., based on infrared light reflected off of the mirror 112 and into the eye tracker 108, FIG. 1B).

The VR system displays (316) a first plurality of frames for virtual-reality images on the display screen using a first persistence in accordance with a first display mode. Persistence is a percentage of a frame duration during which the array of pixels of the display screen is activated. In some embodiments, the first persistence is (318) in a range from 10 to 20 percent. In other words, the array of pixels for the display 104 is activated for 10 to 20 percent of a frame duration, where the frame duration is determined by a refresh rate of the display 104 (e.g., for a refresh rate of 100 Hz, the frame duration for each frame of video data is 10 ms).

Referring now to FIG. 3B, while displaying (316) the first plurality of frames in accordance with the first display mode and while monitoring (314) movement of the user's eye, a saccade of the user's eye is detected (320) (e.g., by eye tracker 108, FIG. 1B).

In some embodiments, detecting (320) the saccade includes (322) determining that the saccade satisfies a movement threshold. In some implementations, the movement threshold is (324) a threshold angle through which the user's eye moves during a specified time period. In some implementations, the threshold angle is (326) approximately 5 degrees (e.g., to within one significant figure). In some implementations, the movement threshold is (328) a threshold speed of the user's eye.

In some embodiments, detecting (320) the saccade includes (330) determining that the saccade satisfies a threshold duration (i.e., detected movement of eye lasts for at least, or more than, a specified duration). In some implementations, the threshold duration is (332) in a range from 60-80 ms.

In some embodiments, detecting (320) the saccade includes determining that the saccade satisfies multiple thresholds (e.g., a movement threshold and a threshold duration).

In response to detecting the saccade, the VR system switches (334) from the first display mode to a second display mode having a second persistence that is greater than the first persistence. In the second display mode, the VR system displays (338) a second plurality of frames for the virtual-reality images using the second persistence. As described previously, by switching to a display mode having a greater persistence during a detected saccade, strobing effects that would other be experienced (at lower persistence) are reduced, and thus the user is provided with a more enjoyable virtual-reality experience. In some embodiments, the second persistence is (336) at least 50 percent (e.g., and the first persistence is in a range from 10 to 20 percent, 318, FIG. 3A).

In some embodiments, the saccade (detected at step 320) is a first saccade. The VR system detects a second saccade while displaying frames in the first mode using the first persistence. The VR system determines that the second saccade does not satisfy the movement threshold. In response to determining that the second saccade does not satisfy the movement threshold, the VR system continues to display frames in the first mode using the first persistence. In other words, even if a saccade is detected, if the saccade does not satisfy a predefined threshold, the VR system does not switch to a display mode having a higher persistence. This may be the case where the magnitude of a detected saccade is not enough for the user to experience the effects of strobing.

In some embodiments, detecting (320) the saccade and switching (334) from the first display mode to the second display mode delays displaying the second plurality of frames using the second persistence by a single frame with respect to a beginning of the saccade. That is, the time it takes to detect the saccade and switch to a higher persistence amounts to a delay (e.g., measured in seconds, frames, etc.) starting from a time at which the saccade begins. In some embodiments, the respective delay associated with detecting (320) the saccade is based in part on a sampling rate (e.g., of the eye tracker 108) used for monitoring movement of the user's eye (e.g., a faster sampling rate decreases the delay for displaying frames using the second persistence).

Referring now to FIG. 3C, in some embodiments, while displaying the second plurality of frames in accordance with the second display mode and while monitoring movement of the user's eye, an end of the saccade is detected (340). Detecting (342) the end of the saccade may include determining that a detected eye movement no longer satisfies a corresponding threshold used for detecting the beginning of the saccade (e.g., a movement threshold). In some implementations, detecting (340) the end of the saccade includes (342) determining that the saccade no longer satisfies the threshold speed of the user's eye.

In response to detecting the end of the saccade, the VR system switches (344) from the second display mode to the first display mode. In the first display mode, a third plurality of frames for the virtual-reality images is displayed (346) using the first persistence (e.g., switch from using 50% persistence to using a 20% persistence). By switching back to the first, lower persistence after a saccade has ended, image blurring that would otherwise result from using the higher persistence in the second display mode is reduced.

In some embodiments, detecting (320, FIG. 3B) the saccade and switching (334) from the first display mode to the second display mode delays displaying the second plurality of frames using the second persistence by a single frame with respect to a beginning of the saccade. Furthermore, detecting (340, FIG. 3C) the end of the saccade and switching (344) from the second display mode to the first display mode delays displaying the third plurality of frames using the first persistence by a single frame with respect to the end of the saccade.

Although some of various drawings illustrate a number of logical stages in a particular order, stages which are not order dependent may be reordered and other stages may be combined or broken out. Furthermore, some stages may be performed in parallel. While some reordering or other groupings are specifically mentioned, others will be apparent to those of ordinary skill in the art, so the ordering and groupings presented herein are not an exhaustive list of alternatives. Moreover, it should be recognized that the stages could be implemented in hardware, firmware, software or any combination thereof.

The foregoing description, for purpose of explanation, has been described with reference to specific embodiments. However, the illustrative discussions above are not intended to be exhaustive or to limit the scope of the claims to the precise forms disclosed. Many modifications and variations are possible in view of the above teachings. The embodiments were chosen in order to best explain the principles underlying the claims and their practical applications, to thereby enable others skilled in the art to best use the embodiments with various modifications as are suited to the particular uses contemplated.

What is claimed is:

1. A method, comprising:
    at a virtual-reality (VR) system that includes a head-mounted display (HMD) system comprising an eye tracker and a display screen comprising an array of pixels:
        monitoring movement of a user's eye, using the eye tracker;
        displaying a first plurality of frames for virtual-reality images on the display screen using a first persistence in accordance with a first display mode, wherein persistence is a percentage of a frame duration during which the array of pixels of the display screen is activated;
        while displaying the first plurality of frames in accordance with the first display mode and while monitoring movement of the user's eye, detecting a saccade of the user's eye; and
        in response to detecting the saccade:
            switching from the first display mode to a second display mode having a second persistence that is greater than the first persistence, and
            in the second display mode, displaying a second plurality of frames for the virtual-reality images using the second persistence.

2. The method of claim 1, wherein the display screen is an organic light-emitting diode (OLED) display.

3. The method of claim 1, wherein detecting the saccade comprises determining that the saccade satisfies a movement threshold.

4. The method of claim 3, wherein the movement threshold is a threshold angle through which the user's eye moves during a specified time period.

5. The method of claim 4, wherein the threshold angle is approximately 5 degrees.

6. The method of claim 3, wherein the saccade is a first saccade, the method further comprising:
detecting a second saccade while displaying frames in the first mode using the first persistence;
determining that the second saccade does not satisfy the movement threshold; and
in response to determining that the second saccade does not satisfy the movement threshold, continuing to display frames in the first mode using the first persistence.

7. The method of claim 3, wherein the movement threshold is a threshold speed of the user's eye.

8. The method of claim 1, wherein detecting the saccade comprises determining that the saccade satisfies a threshold duration.

9. The method of claim 8, wherein the threshold duration is in a range from 60-80 ms.

10. The method of claim 1, wherein:
the display screen has a refresh rate in a range from 75 to 120 Hz; and
the first persistence is in a range from 10 to 20 percent.

11. The method of claim 10, wherein the second persistence is at least 50 percent.

12. The method of claim 1, wherein detecting the saccade and switching from the first display mode to the second display mode delays displaying the second plurality of frames using the second persistence by a single frame with respect to a beginning of the saccade.

13. The method of claim 1, further comprising, at the VR system:
while displaying the second plurality of frames in accordance with the second display mode and while monitoring movement of the user's eye, detecting an end of the saccade; and
in response to detecting the end of the saccade:
switching from the second display mode to the first display mode, and
in the first display mode, displaying a third plurality of frames for the virtual-reality images using the first persistence.

14. The method of claim 13, wherein:
detecting the saccade and switching from the first display mode to the second display mode delays displaying the second plurality of frames using the second persistence by a single frame with respect to a beginning of the saccade; and
detecting the end of the saccade and switching from the second display mode to the first display mode delays displaying the third plurality of frames using the first persistence by a single frame with respect to the end of the saccade.

15. The method of claim 13, wherein:
detecting the saccade comprises determining that a speed of the user's eye satisfies a threshold; and
detecting the end of the saccade comprises determining that the speed of the user's eye no longer satisfies the threshold.

16. The method of claim 1, wherein the HMD system further comprises a mirror to reflect light from the user's eye to the eye tracker.

17. The method of claim 16, wherein the mirror is configured to reflect infrared light and transmit visible light.

18. The method of claim 16, wherein:
the HMD system further comprises a lens and an eye cup coupling the lens to the display screen;
the mirror is within the eye cup; and
the eye tracker is connected to the eye cup.

19. A virtual-reality system, comprising:
a head-mounted display system that includes an eye tracker and a display screen comprising an array of pixels;
one or more processors; and
memory storing one or more programs for execution by the one or more processors, the one or more programs including instructions for:
monitoring movement of a user's eye, using the eye tracker;
displaying a first plurality of frames for virtual-reality images on the display screen using a first persistence in accordance with a first display mode, wherein persistence is a percentage of a frame duration during which the array of pixels of the display screen is activated;
while displaying the first plurality of frames in accordance with the first display mode and while monitoring movement of the user's eye, detecting a saccade of the user's eye; and
in response to detecting the saccade:
switching from the first display mode to a second display mode having a second persistence that is greater than the first persistence, and
in the second display mode, displaying a second plurality of frames for the virtual-reality images using the second persistence.

20. A non-transitory computer-readable storage medium storing one or more programs for execution by one or more processors of a virtual-reality system that includes a head-mounted display system comprising an eye tracker and a display screen comprising an array of pixels, the one or more programs including instructions for:
monitoring movement of a user's eye, using the eye tracker;
displaying a first plurality of frames for virtual-reality images on the display screen using a first persistence in accordance with a first display mode, wherein persistence is a percentage of a frame duration during which the array of pixels of the display screen is activated;
while displaying the first plurality of frames in accordance with the first display mode and while monitoring movement of the user's eye, detecting a saccade of the user's eye; and
in response to detecting the saccade:
switching from the first display mode to a second display mode having a second persistence that is greater than the first persistence, and
in the second display mode, displaying a second plurality of frames for the virtual-reality images using the second persistence.

* * * * *